US009987093B2

(12) United States Patent
Christian et al.

(10) Patent No.: US 9,987,093 B2
(45) Date of Patent: Jun. 5, 2018

(54) SINGLE-MARKER NAVIGATION

(71) Applicant: Brainlab AG, Munich (DE)

(72) Inventors: Georg Christian, Egling (DE); Thomas Feilkas, Kirchseeon (DE); Ingmar Hook, Feldkirchen (DE)

(73) Assignee: Brainlab AG, Munich (DE)

( * ) Notice: Subject to any disclaimer, the term of this patent is extended or adjusted under 35 U.S.C. 154(b) by 38 days.

(21) Appl. No.: 14/902,051

(22) PCT Filed: Jul. 8, 2013

(86) PCT No.: PCT/EP2013/064343
§ 371 (c)(1),
(2) Date: Dec. 30, 2015

(87) PCT Pub. No.: WO2015/003727
PCT Pub. Date: Jan. 15, 2015

(65) Prior Publication Data
US 2016/0135903 A1 May 19, 2016

(51) Int. Cl.
*G06K 9/46* (2006.01)
*G06K 9/62* (2006.01)
(Continued)

(52) U.S. Cl.
CPC ............... *A61B 34/20* (2016.02); *G06K 9/46* (2013.01); *G06K 9/6201* (2013.01);
(Continued)

(58) Field of Classification Search
CPC ............ A61B 34/20; A61B 2034/2065; A61B 2034/2074; A61B 2090/3983; G06T 7/50;
(Continued)

(56) References Cited

U.S. PATENT DOCUMENTS 6,535,756 B1 3/2003 Simon et al.
6,899,675 B2 5/2005 Cline et al.
(Continued)

FOREIGN PATENT DOCUMENTS

DE 4205406 A1 9/1993
DE 102005026654 A1 12/2006
(Continued)

OTHER PUBLICATIONS

International Search Report, No. PCT/EP2013/064343 dated Mar. 27, 2014.
(Continued)

*Primary Examiner* — Jon Chang
(74) *Attorney, Agent, or Firm* — Tucker Ellis LLP

(57) ABSTRACT

A medical data processing method for determining the spatial relationship of a first medical device relative to a second medical device, the method being constituted to be executed by a computer and comprising the following steps: d) acquiring first medical device position data comprising first medical device position information describing the position of the first medical device, wherein the first medical device position data is acquired based on reading, from a marker device having for example a fixed spatial relationship relative to the first medical device, the first medical device position information or information which allows access to the first medical device position information; e) acquiring second medical device position data comprising second medical position information describing the position of the second medical device; f) determining, based on the first medical device position data and the second medical device position data, relative position data comprising relative position information describing the spatial relationship of the second medical device relative to the first medical device.

11 Claims, 3 Drawing Sheets

(51) Int. Cl.
*G06T 7/00* (2017.01)
*A61B 34/20* (2016.01)
*G06T 7/73* (2017.01)
*G06T 7/50* (2017.01)
*G06T 7/246* (2017.01)
*A61B 90/00* (2016.01)

(52) U.S. Cl.
CPC ............ *G06T 7/0012* (2013.01); *G06T 7/246* (2017.01); *G06T 7/50* (2017.01); *G06T 7/73* (2017.01); *A61B 2034/2065* (2016.02); *A61B 2034/2074* (2016.02); *A61B 2090/3983* (2016.02); *G06T 2207/30204* (2013.01)

(58) Field of Classification Search
CPC ......... G06T 7/246; G06T 7/73; G06T 7/0012; G06T 2207/30204; G06T 2207/30004; G06T 2207/30052; G06K 9/46; G06K 9/6201; G06K 2017/009; G06K 2209/05; G06K 2209/057
See application file for complete search history.

(56) References Cited

U.S. PATENT DOCUMENTS

| | | |
|---|---|---|
| 6,978,167 B2 | 12/2005 | Dekel et al. |
| 7,033,360 B2 | 4/2006 | Cinquin et al. |
| 7,213,598 B2 | 5/2007 | Zeiss et al. |
| 7,542,791 B2 | 6/2009 | Mire et al. |
| 7,726,564 B2 | 6/2010 | Goldbach |
| 7,728,280 B2 | 6/2010 | Feilkas et al. |
| 7,794,394 B2 | 9/2010 | Frangioni |
| 2003/0208125 A1 | 11/2003 | Watkins |
| 2004/0230199 A1 | 11/2004 | Jansen et al. |
| 2005/0027304 A1 | 2/2005 | Leloup et al. |
| 2005/0251186 A1 | 11/2005 | Revie et al. |
| 2006/0173356 A1 | 8/2006 | Feilkas |
| 2008/0281334 A1 | 11/2008 | Zheng et al. |
| 2012/0078236 A1* | 3/2012 | Schoepp ................ A61B 5/061 606/1 |
| 2013/0108979 A1 | 5/2013 | Daon |
| 2014/0272773 A1* | 9/2014 | Merritt ................ A61B 5/0088 433/29 |
| 2018/0055579 A1* | 3/2018 | Daon ..................... A61B 34/20 |

FOREIGN PATENT DOCUMENTS

| | | |
|---|---|---|
| DE | 102007028731 A1 | 1/2009 |
| DE | 102010041564 A1 | 3/2012 |
| EP | 1138256 A2 | 4/2001 |
| EP | 1719472 A1 | 3/2008 |
| EP | 1933276 B1 | 6/2010 |
| EP | 1952779 B1 | 4/2012 |
| GB | 2473305 A | 9/2011 |
| WO | 9641481 A1 | 12/1996 |
| WO | 9729710 A1 | 8/1997 |
| WO | 9938449 A1 | 8/1999 |
| WO | 0047103 A2 | 8/2000 |
| WO | 0101854 A2 | 1/2001 |
| WO | 0167979 A1 | 9/2001 |
| WO | 0237935 A2 | 5/2002 |
| WO | 03043485 A2 | 5/2003 |
| WO | 2004001569 A2 | 12/2003 |
| WO | 2004030560 A2 | 4/2004 |
| WO | 2005000129 A1 | 1/2005 |
| WO | 2005102202 A1 | 11/2005 |
| WO | 2006060631 A1 | 6/2006 |
| WO | 2008071014 A1 | 6/2008 |
| WO | 2008103273 A2 | 8/2008 |
| WO | 2010145858 A1 | 12/2010 |
| WO | 2011020505 A1 | 2/2011 |
| WO | 2013053397 A1 | 4/2013 |

OTHER PUBLICATIONS

International Preliminary Report on Patentability, No. PCT/us2013/064343 Dated Jan. 12, 2016.

* cited by examiner

SINGLE-MARKER NAVIGATION

Related Application Data

This application is a national phase application of International Application No. PCT/EP2013/064343 filed Sep. 25, 2012 and published in the English language.

The invention is directed to a medical data processing method for determining the position of a first medical device relative to a second medical device and in particular to a medical marker device, a positioning guide for positioning a tool relative to a medical implant and a system for determining the position of a medical tool relative to a medical implant.

When attaching a medical implant such as a femoral plate to an anatomical structure such as a femur in order to for example join together a femur fracture, conventionally a fastener such as a screw or a nail is used to fix the femoral plate to the femur. To this end, implant attachment units such as holes in the femoral plate through which the fasteners are inserted into the anatomical structure are provided at predetermined positions on the medical implant. These positions generally depend on the type, in particular the size and/or shape, and/or envisaged use, of the medical implant. When attaching the medical implant to the anatomical structure it therefore is necessary to know the positions of the attachment units in order to be able to insert the fasteners at the correct positions.

Known solutions to this problem include providing an incision in the patient's skin down to the anatomical structure to which the medical implant is to be fastened so that the medical implant is visible to the outside throughout the procedure. However, such an approach involves large surgical effort and is associated with numerous health risks. Alternatively, a positioning guide which remains outside of the patient's body throughout the procedure and has a predetermined and preferably fixed spatial relationship relative to the medical implant may be used in such a procedure. The positioning guide preferably has markings on its surface which indicate the positions of the attachment units on the medical implant. This approach allows for only a small incision through which a preferably small dimension of the medical implant may be inserted which minimizes health risks to the patient while allowing to determine the positions of the implant attachment units from outside the patient's body. One shortcoming of such an approach is that such a positioning guide may generally be used only with a single type of medical implant since the markings on the surface of the positioning guide have to uniquely describe the positions of the implant attachment units. Providing such a positioning guide therefore is not cost-efficient since a medical institution such as a hospital may have to keep different types of positioning guides on store for use with corresponding different types of medical implants.

A problem to be solved with the invention thus is to provide in particular a marker device and a positioning guide for supporting positioning a tool relative to a medical implant which can be flexibly used with different types of implants while reducing health risks to the patient, and to provide a medical data processing method which supports positioning of a tool relative to a medical implant by taking advantage of in particular the properties of the mentioned positioning guide.

This problem is solved by the subject-matter of any appended independent claim. Advantages, advantageous features, advantageous embodiments and advantageous aspects of the present invention are disclosed in the following and contained in the subject-matter of the dependent claims. Different advantageous features can be combined in accordance with the invention as long as technically sensible and feasible. In particular, a feature of one embodiment which has the same or similar function of another feature of another embodiment can be exchanged. In particular, a feature of one embodiment which supplements a further function to another embodiment can be added to the other embodiment.

EXEMPLARY SHORT DESCRIPTION OF THE PRESENT INVENTION

In the following, a concise description of the present invention is offered which is to be considered merely as an example and not as a limitation of the invention to the features described in the following.

The present invention provides in particular a marker device and, as a separate aspect of the invention, a positioning guide for supporting positioning of a tool such as a drill or a screwdriver relative to a medical implant such as a femoral plate.

The marker device can be advantageously detected by a navigation system operating on the principle of image analysis-based video tracking The marker device advantageously describes information which describes an implant attachment unit of the medical implant. For example, the marker device is a two-dimensional marker device which provides image-detectable information which describes the positions of holes in the medical implant in particular relative to the at least one marker device.

The positioning guide is preferably provided with at least one such marker device. The positioning guide advantageously has a predetermined and preferably fixed spatial relationship relative to the medical implant in particular determining a spatial orientation of the tool driving unit relative to the medical implant for attaching the medical implant to an anatomical structure. For example, the at least one marker device provides information to a navigation system and therefore to a user on how to position and orient a drill relative to the medical implant and in particular also the anatomical structure in order to drill holes into the anatomical structure which serve to attach the medical implant to the anatomical structure. The positioning guide serves in particular to guide, in particular position, a tool and preferably a tool driving unit relative to the medical implant. Such a tool driving unit is in particular configured to drive a tool, which tool is suitable to machine an anatomical structure or to attach a medical implant to an anatomical structure. The tool driving unit may for example be at least one of a drill and a screwdriver which is configured to drill a hole into a structure or to drive a fastener such as screw, respectively, in order to fasten the medical implant to an anatomical structure. Additionally or alternatively, the tool driving unit may also be a driven hammer for driving e.g. a nail into a structure in order to attach the medical implant to an anatomical structure.

The invention preferably also provides a medical data processing method which provides in particular graphical information to a user on how to position and orient a tool relative to the medical implant and in particular relative to the anatomical structure in preparation of a procedure which is directed to, but does not necessarily comprise, fastening the medical implant to the anatomical structure. The graphical information is determined based on detecting the marker devices provided on the positioning guide.

The invention is further directed to a method which allows to aim a tracked tool at a medical device based on information about the geometry of the medical device and the spatial relationship of the marker device relative to the medical device.

GENERAL DESCRIPTION OF THE INVENTION

In this section, a general description of the features and embodiments of the present inventions is offered. The features described in the following constitute preferred and particular features of the invention.

The invention is directed to in particular a medical marker device (also denoted simply as "marker device") having the following preferred features. The marker device preferably describes, in particular comprises, information usable for navigation, in particular determining positions, in a medical procedure. The positional information is defined in particular relative to the marker device itself. The information is in particular positional information or at least allows access to positional information. Preferably, the positional information is first medical device position information. The marker device preferably describes (in particular comprises) the first medical device position information (also denoted as only "medical device position information"). According to a very preferred embodiment, the marker device comprises a graphical feature which is present on in particular at least one of its exterior surfaces and is detectable by an optical detection unit (e.g. a camera) and can be determined in particular by image data analysis based on the optical detection and which describes (in particular comprises and/or represents) the positional information, in particular the first medical device position information. The graphical pattern is applied for example as a printed label or is present as a structural feature of the marker device, for example as an etched graphical pattern. Preferably, at least one marker device, further preferably exactly (more preferably, only) one marker device is required in order to describes the first medical device position information. In particular, only a single marker device describing (in particular comprising) the first medical device position information is, in particular needs to be, detected. However, acquiring the first medical structure position information can also be described by a plurality (in particular an array) of markers. The marker device advantageously is a two-dimensional marker device. However, the marker device may alternatively be embodied by a plurality of retroreflective marker spheres having for example a predetermined spatial relationship relative to one another.

The first medical device position information describes in particular the position of a first medical device (also denoted as only "medical device") and/or allows access to information about the position of the first medical device. The information about the position of the first medical device may be for example metadata such as information about the type of the first medical device which is associated with information about the position of the first medical structure which is stored in a database and can be accessed by the inventive method. The first medical device position information preferably describes the position of the first medical device relative to the position of the marker device or at least allows access to information describing the position of the first medical device relative to the position of the marker device. The first medical device position information is preferably embodied by a transformation representing in particular a coordinate transformation (more particularly, a mapping) between the position of the marker device and the position of the first medical device. The arithmetic function defining the transformation is predetermined and preferably known for each type of first medical device and is preferably encoded in the graphical pattern represented by the marker device. At least, information describing the transformation is stored in the aforementioned database such that it is accessible based on the first medical device position information.

The marker device preferably is a two-dimensional marker device, for example an image-detectable marker device which in particular comprises a as a graphical feature a graphical pattern for image data analysis (in particular, image data evaluation, preferably evaluation of digital image data, in particular by applying an image segmentation algorithm to the image data). Preferably, the marker device comprises a planar substrate, for example only one planar substrate, which carries the graphical feature. The planar substrate is preferably attached to for example the first medical device. The substrate can be for example a label (in particular an adhesive label) or a tag. The substrate is in particular a structure which rests relative to all parts of the marker device representing information (in particular the first medical device position information), in particular to which all these parts of the marker device are attached with a preferably fixed spatial relationship relative to the substrate.

In particular, the marker device is a two-dimensional code such as a two-dimensional bar code or a QR-code® which is in particular attached to the marker carrying unit. For example, the two-dimensional code is printed on a label which is adhered, in particular stuck, to the marker carrying unit of the positioning guide described further below.

A QR-code® comprises in particular a quadratic matrix of dots which represent the coded information (i.e. the information coded in the code) in a binary manner. A special marking in three of the four corners of the square defines the orientation of the QR-code®. The data included in a QR-code® are protected by an error-correcting code. This enables to tolerate a loss of up to 30% of the coded information, i.e. the QR-code® can still be decoded if at least 70% of the information is recovered. The information is coded in the form of dots of in particular two colours which have a preferably high contrast, for example black and white dots. The coded information is recovered in particular by scanning the QR-code® for example with a camera (in particular digital camera) which is connected to a computer, in particular a digital processor, which is configured to execute a program for interpretation of the image information representing the QR-code®, i.e. for analysis (evaluation) of the corresponding image data, and then executing the program for interpreting the image information. The camera advantageously is the camera of a mobile device such as a mobile phone or a PDA (personal digital assistant). The computer is in particular a computer (more particularly, a digital processor) which is part of such a mobile device, preferably is the control unit used to control the functions of the mobile device. The camera then functions as a scanner (also termed "imager") which scans the two-dimensional code, which in the framework of the present invention represents the two-dimensional marker device and/or is included in the marker device.

Alternatively or additionally, the marker device may be represented by a three-dimensional marker device such as reference star carrying in particular three for example retroreflective marker spheres which have a preferably predetermined and advantageously fixed spatial relationship (in particular position and/or orientation) relative to one another. The reference star comprises a base part which is attached to the marker carrying unit in particular with a predetermined and advantageously a fixed spatial relationship (position and/or orientation) relative to the marker carrying unit. Such a three-dimensional marker device can also comprise as a graphical feature a graphical pattern for optical detection and in particular image evaluation, the pattern being defined in particular by the distance of the marker spheres relative to one another. Advantageously, the information about the spatial relationship of the marker spheres relative to one another represents a code describing the first medical device position information.

The first medical device position information is preferably encoded by the graphical pattern defined by (in particular, included in) the marker device. In the case of a two-dimensional marker device, such a graphical pattern is for example the pattern contained in a bar code or a QR-code®, in the case of a three-dimensional marker device the graphical pattern is preferably represented by the spatial relationship (in particular position and/or orientation) of for example marker spheres contained in the marker device relative to one another (in particular, by their graphical appearance in in particular a two-dimensional image of the three-dimensional marker device). In a further embodiment, the marker device preferably comprises a marker array of marker devices, i.e. a plurality of marker devices (in particular exactly or at least two marker devices). In that case, the implant attachment unit information can also be described by the marker array, i.e. by the spatial relationship (in particular, position and/or orientation) of the plurality of marker devices relative to one another. In particular, the implant attachment unit information is then described by the graphical pattern defined by the two-dimensional appearance of the marker array of marker devices in an image of the marker array.

The first medical structure may be any of an anatomical structure (e.g. an external or an internal body part of a patient's body) and a medical device (e.g. an implant or a tool, in particular a medical tool such as a medical instrument, or any other device which is used in connection with a medical procedure).

If the first medical structure is a medical device, the first medical structure position data is preferably embodied by first medical device position data comprising first medical device position information which describes a position of the first medical device. The first medical device position data is preferably acquired based on reading, from the marker device, the first medical device position information or information which allows access to the first medical device position information. The marker device for example has a fixed spatial relationship relative to the first medical device.

For example, the first medical structure is an implant attachment unit and the first medical device position data comprises in particular implant attachment unit data, wherein the first medical device position information comprises in particular implant attachment unit information describing an implant attachment unit. The implant attachment unit data is acquired in particular based on detecting a graphical pattern represented by an image (in particular two-dimensional image information) of the marker device which is advantageously attached to the positioning guide. In particular, the image (more particularly, the two-dimensional image information) describes the marker device, in particular the outer (visual) appearance of the marker device. For example, the implant attachment unit information describes the type of the medical implant for which the positions of the implant attachment units are known in particular relative to preferably predetermined positions on the marker carrying unit at which each one of a plurality of marker devices is attached to the marker carrying unit. Alternatively or additionally, the implant attachment unit information describes at least one of the position of the implant and the position of the implant attachment unit. Information about the positions of the implant attachment units is preferably stored in a database and can be accessed based on the implant attachment unit information about the type of implant which is acquired based on detecting the marker device.

The implant attachment unit preferably comprises at least one part, i.e. a part or a plurality of parts, of a medical implant. The implant attachment unit in particular serves to attach the implant to an anatomical structure. For example, the implant is a femoral plate and the anatomical structure is a femur. As another example, the implant is part of a knee endoprosthesis, for example a part to be fitted on the distal end of the femur or on the proximal end of the tibia, end the anatomical structure is the distal end of the femur or the proximal end of the tibia, respectively. More particularly, the implant attachment unit provides a fixture for a fastener (in particular a clearance or recess for receiving a fastener) with which the implant can be (in particular is) attached or fastened, respectively, to the anatomical structure. Such a fixture in particular holds the fastener, for example the fixture is at least one hole (or a plurality of holes) for generating e.g. a form fit with a fastener, wherein the fastener in particular is at least one of a screw and a nail.

The invention is further directed to a positioning guide which is preferably constituted to support positioning of the aforementioned medical tool relative to a medical implant. The positioning guide preferably comprises a marker carrying unit provided with at least one marker device, wherein the marker device preferably is the above-described marker device. Furthermore, the positioning guide preferably comprises a connecting section for connecting the marker carrying unit to the implant with a predetermined and preferably fixed spatial relationship, in particular at least one of position and orientation, relative to the implant. The marker carrying unit and the connecting section may be formed integrally. Alternatively, they may be formed separately, i.e. the marker carrying unit and the connecting section may be formed as separate physical structures which for intended use of the positioning guide have to be fastened to each other. The marker carrying unit preferably has an elongated shape, for example the shape of a bar, however other shapes such as a planar or circular shape are also within the framework of the invention. Preferably, the marker carrying unit and the connecting section have an L-shape at least during intended use of the positioning guide. If the marker carrying unit and the connecting section are formed integrally, i.e. as a single part, they preferably together have an L-shape. The longer leg of the L is then preferably formed by the marker carrying unit, and the shorter leg of the L is then preferably formed by the connecting section. However, the positioning guide may also be configured vice versa, i.e. the shorter leg of the L may be formed by the marker carrying unit and the longer leg of the L may be formed by the connecting section. Preferably, the connecting section is removably attachable to the medical implant. For example, the connecting section may be screwed to the medical implant or slid onto a part of the medical implant so as to be held by for example form fit.

The invention is further directed to a system comprising at least one of the medical tool and a tool driving unit for driving the medical tool and a detection unit for detecting a marker device (in particular, the above-described marker device) which is in particular attached to the aforementioned positioning guide. The medical tool is preferably suitable to a machine (in particular, at least one of drill and cut) an anatomical structure (in particular a bony structure such as a part of the femur or the tibia). For example, the tool is a drill or a saw. Alternatively or additionally, the tool is preferably suitable to attach a medical implant to an anatomical structure. For example, the tool is a screw driver or a driven hammer for driving a screw in particular through the implant attachment unit into the anatomical structure in order to attach the medical implant to the anatomical structure. As a further example, the tool may be a hammer suitable to drive a nail in particular through the implanted attachment unit into the anatomical structure. The tool driving unit includes for example a motor which is configured to drive, in particular move, the tool in order to apply the tool as desired. The detection unit is in particular a camera unit such as for example the aforementioned camera for imaging the graphical pattern defined by the marker device. The tool or the tool driving unit, respectively, and the detection unit preferably have a predetermined and advantageously fixed spatial relationship relative to each other. For example, the tool or tool driving unit, respectively, and the detection unit are located in a common housing. As a further example, the tool or tool driving unit, respectively, may be fitted with a holding unit for holding the detection unit, in particular it may be fitted with a frame for holding a digital camera (in particular, for holding a mobile device such as a mobile phone which includes a digital camera). The detection unit preferably has a spatial relationship, in particular at least one of position and orientation, relative to the tool driving unit such that its detection area (i.e. the area in which detection of the at least one marker device is possible) points into the same direction as a tool in particular if it is attached to the tool driving unit for being driven. This provides the advantage that the tool driving unit and the tool can be pointed towards at least one of the positioning guide and the medical implant while at the same time the detection unit is able to detect the marker device.

Preferably, the detection unit is operatively connected to a data processing device such as a computer or at least a microprocessor, both of which are preferably installed in at least one of the aforementioned mobile devices in order to execute the following medical image data processing method which is also part of the invention.

This data processing method is in particular a medical data processing method for determining the spatial relationship (in particular at least one of the position and the orientation) of a first medical device relative to a second medical device (which is in particular other than or different from the first medical device). The first medical device is the second medical device are in particular any medical device (e.g. an implant or a tool, in particular a medical tool such as a medical instrument, or any other device which is used in connection with a medical procedure).

In accordance with this data processing method, preferably first medical device position data comprising first medical device position information is acquired based on (in particular by i.a.) detecting a marker device (in particular at least one of its position and information described by, in particular contained in, the marker device), in particular based on detecting a graphical feature of the marker device, in particular graphical pattern represented by an image (in particular a two-dimensional image) of the marker device which is advantageously attached to the first medical device with a preferably predetermined and preferably fixed spatial relationship (in particular at least one of position and orientation) relative to the first medical device. The marker device preferably describes (in particular comprises) the first medical structure position data (in particular, the first medical device position information). The marker device preferably is the marker device described above. According to a very preferred embodiment, the marker device comprises a graphical feature which is present on in particular at least one of its exterior surfaces and is detectable by an optical detection unit (e.g. a camera) and can be determined in particular by image data analysis based on the optical detection and which describes (in particular comprises and/or represents) the positional information, in particular the first medical structure position information. The first medical device position information is then determined based on in particular detecting the graphical feature on the marker device with the optical detection unit and advantageously analyzing image data generated based on the detection result (e.g. by applying an image segmentation algorithm to the image data). In particular, the first medical device position data is acquired based on reading, from the marker device, the first medical device position information or information which allows access to the first medical device position information. The graphical pattern is applied for example as a printed label or is present as a structural feature of the marker device, for example as an etched graphical pattern. Preferably, at least one marker device, further preferably exactly (more preferably, only) one marker device is, in particular has to be, detected. In particular, only a single marker device describing (in particular comprising) the first medical device position data is, in particular needs to be, detected. However, acquiring the first medical device position data can also be based on detecting a plurality of markers. The marker device has for example a fixed spatial relationship relative to the first medical device. The marker device advantageously is the above-described two-dimensional marker device. However, the marker device may alternatively be embodied by a plurality of retroreflective marker spheres having for example a predetermined spatial relationship relative to one another, wherein the information about the spatial relationship represents a code describing the first medical structure position information.

The first medical device position information describes in particular the position of a first medical device and/or allows access to information about the position of the first medical device. The information about the position of the first medical structure may be for example metadata such as information about the type of the first medical device which is associated with information about the position of the first medical device which is stored in a database and can be accessed by the inventive method. The first medical device is for example an implant attachment unit and the first medical structure position data comprises in particular implant attachment unit data, wherein the first medical device position information comprises in particular implant attachment unit information describing an implant attachment unit. The implant attachment unit data is acquired in particular based on detecting a graphical pattern represented by an image (in particular a two-dimensional image) of the marker device which is advantageously attached to the positioning guide. In particular, the image (more particularly, the two-dimensional image information) describes the marker device, in particular the outer (visual) appearance of the marker device. The implant attachment unit data comprises in particular the aforementioned implant attachment unit information. For example, the marker device describes the type of the medical implant, for which the positions of the implant attachment units are known in particular relative to preferably predetermined positions on the marker carrying unit at which each one of a plurality of marker devices is attached to the marker carrying unit. Information about the positions of the implant attachment units is preferably stored in the aforementioned database and can be accessed based on the implant attachment unit information about the type of implant which is acquired based on detecting the marker device.

Preferably, second medical device position data is acquired which comprises second medical device position information describing the position of the second medical device. The second medical device is for example a tool and the second medical device position data comprises in particular tool position data, wherein the first medical structure position information comprises in particular tool position information describing the position of a tool. The second medical device position information, in particular the tool position information, describes in particular the spatial relationship, in particular at least one of position and orientation, of the tool relative to a coordinate system in which the position of the detection unit is defined. Preferably, the second medical device has a predetermined (in particular known) and preferably fixed spatial relationship (in particular at least one of position and orientation) relative to the detection unit which is used to detect the marker device. In particular, the spatial relationship of the second medical device is defined relative to the detection unit.

Preferably, relative position data is determined based on the first medical device position data (in particular based on the implant attachment unit data) and the second medical device position data (in particular based on the tool position data). The relative position data comprises in particular relative position information which describes in particular the spatial relationship, in particular at least one of the position and the orientation, of the second medical device relative to the first medical device. Further preferably, determining the relative position data comprises determining graphical position output data which comprises graphical position output information. In particular, the graphical position output information describes the spatial orientation, in particular at least one of position and orientation, of the second medical device in particular relative to the first medical structure in a graphical output, in particular in image information (specifically, in an image such as a camera image). The graphical output is preferably output by a navigation information output unit which is preferably operatively coupled to at least one of the detection unit and the computer (in particular processor) executing the inventive data processing method. The navigation information output unit comprises in particular a navigation output unit such as an image output device like a monitor in which the graphical output used for rendering the graphical position output information is provided. Preferably, the detection unit and the navigation output unit are combined in single device, for example one of the aforementioned mobile devices, preferably in a mobile phone. In particular, the detection unit is the camera and the navigation output unit is the monitor (i.e. the display) of such a mobile phone. The graphical position output information is embodied by for example a graphical output which is rendered as an image feature in the image information provided based on processing the detection result of the detection unit, in particular in an image of in particular the marker device and preferably also the marker carrying unit which is taken by the camera. For example, such an image feature is overlaid on the mentioned camera image. Thereby, a user gets an impression of for example where the second medical device, in particular the tool or a tool driving unit (in particular, the tool attached to the tool driving unit), is currently pointing.

It is preferably also determined whether the relative position information describes a position of the second medical device (in particular the tool) relative to the first medical device (in particular the implant attachment unit) which fulfills a predetermined condition. Such a predetermined condition can for example be defined as at least one of a distance (in particular, two-dimensional distance) between the position of the second medical device and the position of the first medical device and an angle (in particular, three-dimensional angle) of orientation between the first and second medical device (in particular relative to a central axis of the implant attachment unit such as the axis of rotation of an in particular circular hole for receiving a screw) which may not be exceeded. Advantageously, it is determined whether the second medical device (in particular the tool driving unit and/or the tool) points at a position which is identical to the position of the first medical device (in particular the implant attachment unit). In other words, it is in particular determined whether the second medical device (in particular the tool and/or the tool driving unit) is pointing towards the first medical device (in particular the implant attachment unit). In order to support the user in correspondingly orienting and positioning the tool driving unit and/or the tool, the position of the implant attachment unit can also be rendered in the aforementioned graphical output. The graphical output information is then preferably modified, in particular highlighted, if the predetermined condition is fulfilled, in particular if the tool driving unit and/or the tool is pointing towards the position of the implant attachment unit. As described above, the information about the position of the implant attachment unit is preferably determined based on the implant attachment unit information. Highlighting the graphical output information may be achieved by for example changing the colour of the graphical output feature (which is in particular the above-described image feature) or the graphical output features representing at least one of the orientation of the tool driving unit and/or the tool (i.e. the position in the image towards which the tool driving unit and/or the tool are pointing) and the position of the implant attachment unit. Alternatively or additionally, highlighting may be achieved by rendering the respective graphical output features in a flashing manner.

The invention is also directed to a program which, when running on a computer or when loaded onto a computer, causes the computer to perform the method steps according to any one of the preceding claims and/or a program storage medium on which the program is stored in particular in a non-transitory form and/or a computer, in particular a cloud computer or a computer installed in a mobile device such as a mobile phone, on which the program is running or into the memory of which the program is loaded and/or a signal wave, in particular a digital signal wave, carrying information which represents the program, in particular the aforementioned program, which in particular comprises code means which are adapted to perform the method steps according to any one of the preceding four claims.

Furthermore, the invention is also directed to a system comprising at least one of the above-described positioning guide and the system comprising at least one of the medical tool and the tool driving unit and the detection unit and the above-described medical implant which is connectable, in particular connected, to the connecting section of the positioning guide.

The invention is furthermore also directed to a method which is described in the following.

Preferably, a marker device (in particular, the above-described marker device) is provided which has a preferably fixed special relationship relative to a medical device (which can be embodied by in particular the above-described first medical device). The marker device is for example video-readable (i.e. in particular detectable by an optical detection means which detects optical information in the visible wavelength spectrum which is in particular represented by an electromagnetic wavelength interval from about 400 nm to about 800 nm) and preferably comprises the above-described planar substrate, for example only one planar substrate, which carries a graphical feature. The planar substrate is preferably attached to for example a medical device.

Preferably, information about the geometry of the medical device and information about the spatial relationship of the marker device relative to the medical device is acquired. There are different ways of acquiring the information about the geometry of the medical device so that the information is acquired for example based on at least one of:

Analysing an image of the medical device and the marker device (for example by applying an image segmentation algorithm to such an image) and comparing the results of the image analysis with predetermined information about the geometry of a plurality of medical devices. The information about the geometry of a plurality of medical devices is preferably contained in a database which is polled, in order to acquire the information about the geometry of the medical device.

Identifying the medical device by calibrating or analysing it with a tracked calibration device (for example a calibration device which is dimensioned to mechanically fit to the medical device in a characteristic manner in order to determine the type of medical device and preferably also the position of the medical device). The result of identifying the medical device is preferably compared with predetermined information about the geometry of a plurality of medical devices (which is for example contained in the aforementioned database), in order to acquire the information about the geometry of the medical device.

Using a first tracked tool to sample the geometry of the medical device, the first track tool being for example a pointer device (which essentially is for example a rod having a marker device touched to it, wherein in particular the tip of the rod has a predetermined, fixed and known spatial relationship relative to the marker device. The geometry of the medical device is sampled for example based on at least one of:

1. Identifying specific points on the surface of the medical device which describe the information about the geometry of the medical device and comparing the results of identifying the points with predetermined information about the geometry of a plurality of medical devices which is contained in a database (in particular the aforementioned database), in order to acquire the information about the geometry of the medical device.

2. Acquiring a point cloud (i.e. a set of in particular discrete and non-overlapping positions in space) describing (in particular representing) points on the surface of the medical device, and interpolating between the points. At least the position of the marker device is preferably acquired by acquiring the point cloud. The point cloud is then preferably compared with predetermined information about the geometry of a plurality of medical devices which is contained in a database (in particular the aforementioned database), in order to acquire the information about the geometry of the medical device.

3. In particular in case the geometry (in particular the shape) of the medical device is not accessible (for example if the shape is comparably complex or must for reasons of for example sterility not be touched with the first tracked tool), the trajectories necessary for fixing the medical device (in particular an implant) to an anatomical structure (such as for example a bone) are advantageously taught-in one-by-one, i.e. the directions in which the medical device is to be fastened are identified (for example by using the first track tool) and acquired individually by for example notifying them to a navigation system. This results in acquiring information about the position of a part of medical device which is useable to fasten the medical device to a structure such as in particular to an anatomical body part.

Then, a second tracked tool such as for example a drill is aimed at a part (for example an implant attachment unit) of the medical device (which for example is an implant) based on the information about the geometry of the medical device and the spatial relationship of the marker device relative to the medical device. The second track tool is in particular aimed along the aforementioned trajectories along which the medical device is to be fastened.

According to an embodiment of this method, the information about the geometry of the medical device (which is also termed specific medical device) is acquired based on at least one of:

Analysing an image of the medical device and the marker device and comparing the result of the image analysis with predetermined information about the geometry of the plurality of medical devices which is contained in a database, in order to acquire the information about the geometry of the medical device as described above.

Identifying the medical device by calibrating or analysing it with a tracked calibration device and comparing the result of identifying the medical device with predetermined information about the geometry of a plurality of medical devices which is contained in a database in order to acquire the information about the geometry of the medical device (as described above).

Using a first track tool to sample the geometry of the medical device based on at least one of identifying specific points on the surface of the medical device and acquiring a point cloud as described above.

The aforementioned steps of comparing then preferably include determining whether the predetermined information contains a set of information about the geometry of a medical device which has a geometry (in particular at least one of size—in particular volume—and shape) which at least lies within a predetermined neighbourhood of the geometry of the specific medical device and preferably is equal to the geometry of the specific medical device. The information about the geometry of the specific medical device is preferably determined to be the geometry of the medical device described by such a set of information which is contained in the database. The geometry of the medical device described by the set of information contained in the data basis is then for example substituted as the geometry of the specific medical device (corresponding to for example the first medical device).

Using the pointer as described above preferably comprises using the pointer to notify the positions of specific parts of the medical device to a navigation system. The geometry of the medical device is then preferably determined based on the notified positions.

Within this method, the marker device is preferably tracked by a tracking device which is comprised in for example a handheld device, in particular a mobile media player or a mobile phone, and which include the camera (in particular a digital camera, specifically a digital video camera) which is sensitive for example in the visual wavelength range.

The medical device preferably includes a drill guide or an implant, and the second tracked tool is preferably configured to include a drill or a screw driver. Furthermore, the second track toll preferably has a fixed spatial relationship relative to at least one of the tracking device for tracking the marker device (such as for example the relevant at least part of the aforementioned handheld device) and a display device for displaying the results of the tracking (such as for example a monitor included and/or operatively connected to the aforementioned handheld device). The first tracked tool and the tracking device for example share a common housing, in particular they are disposed in a single (common) housing.

According to an alternative embodiment, the second tracked tool does not have a fixed spatial relationship relative to at least one of the aforementioned tracking device for tracking the marker device and the aforementioned display device for displaying the results of the tracking In that case, the second tracked tool is preferably associated with a further marker device (which is preferably fastened to the second track tool). The second track tool and the further marker device then preferably have a fixed relationship relative to one another.

In particular, the invention does not involve, in particular it does not comprise or encompass, an invasive step which would represent a substantial physical interference with the body requiring professional medical expertise to be carried out and entailing a substantial health risk even when carried out with the required professional care and expertise. In particular, the invention does not comprise a step of placing the medical implant in position for fastening it to the anatomical structure or a step of fastening the medical implant to the anatomical structure or a step of preparing the anatomical structure for being fastened to the medical implant. More particularly, the invention does not involve (in particular comprise or encompass) any surgical or therapeutic activity. Rather, the invention is directed to in particular positioning the tool relative to the medical implant, which may be present outside of the patient's body. For at least this reason, no surgical or therapeutic activity (in particular no surgical or therapeutic step) is necessitated or implied by carrying out the invention.

The invention is directed to the following preferred embodiments:

A. A medical data processing method for determining the spatial relationship of a first medical structure relative to a second medical structure, the method being constituted to be executed by a computer and comprising the following steps:

a) acquiring, based on detecting a marker device, first medical structure position data comprising first medical structure position information describing the position of the first medical structure;

b) acquiring second medical structure position data comprising second medical structure position information describing the position of the second medical structure;

c) determining, based on the first medical structure position data and the second medical structure position data, relative position data comprising relative position information describing the spatial relationship of the second medical structure relative to the first medical structure.

B. The method according to the preceding embodiment, wherein detecting the marker device (22) comprises detecting a graphical feature of the marker device.

C. The method according to any one of the preceding embodiments, wherein determining the relative position data comprises determining graphical position output data comprising graphical position output information describing the spatial relationship of the tool relative to the implant attachment unit in a graphical output, in particular a camera image.

D. The method according to any one of the two preceding embodiments, wherein it is determined whether the position of the second medical structure relative to the first medical structure fulfils a predetermined condition, and wherein the graphical position output information is modified, in particular highlighted, if the predetermined condition is fulfilled.

E. The method according to any one of the preceding embodiments, wherein the first medical structure is an anatomical structure or a medical device and wherein the second medical structure is an anatomical structure or a medical device.

F. The method according to any one of the preceding embodiments, wherein the second medical structure has a predetermined and preferably fixed spatial relationship relative to a detection unit which is used to detect the marker device.

G. The method according to any one of the preceding embodiments, wherein the first medical structure is an implant attachment unit and the second medical device is a tool, wherein the first medical structure position data comprises implant attachment unit data and wherein the first medical structure position information comprises implant attachment unit information describing the implant attachment unit, and wherein the second medical structure position data comprises tool position data and wherein the second medical structure position information comprises tool position information describing the position of the tool.

H. A program which, when running on a computer or when loaded onto a computer, causes the computer to perform the method steps according to any one of the preceding embodiments and/or a program storage medium on which the program is stored in particular in a non-transitory form and/or a computer, in particular a cloud computer or a computer installed in a mobile device such as a mobile phone, on which the program is running or into the memory of which the program is loaded and/or a signal wave, in particular a digital signal wave, carrying information which represents the program, in particular the aforementioned program, which in particular comprises code means which are adapted to perform the method steps according to any one of the preceding four embodiments.

I. A medical marker device describing medical structure position information or information allowing access to medical structure position information, the medical structure position information describing the position of a medical structure.

J. The marker device according to the preceding embodiment, comprising a graphical pattern which describes the medical structure position information.

K. The marker device according to any one of the two preceding embodiments, wherein the medical structure position information describes the position of a medical structure relative to the position of the marker device.

L. The marker device according to any one of the three preceding embodiments, wherein the marker device is a two-dimensional marker device, for example an image-detectable marker device which in particular comprises a graphical pattern for image data analysis.

M. The marker device according to any one of the four preceding embodiments, wherein the marker device comprises a marker array of marker devices and wherein the marker array describes the implant attachment unit information.

N. The marker device according to any one of the five preceding embodiments, wherein the medical structure position information comprises implant attachment unit information describing an implant attachment unit of a medical implant.

O. The marker device according to the preceding embodiment, wherein the implant attachment unit comprises a part or a plurality of parts of the implant with which the implant is to be attached to an anatomical structure, in particular a fixture for a fastener, in particular a clearance or recess for receiving at least one of a screw and a nail.

P. The marker device according to any one of the three preceding embodiments, wherein the implant attachment unit information describes at least one of the type of implant, the position of the implant, and the position of the implant attachment unit in particular relative to the marker device.

Q. A positioning guide for positioning of a medical tool relative to a medical implant, comprising:

a) a marker carrying unit provided with at least one marker device according to any one of the eight preceding claims; and b) a connecting section for connecting the marker carrying unit to the implant.

R. A system for determining the position of a medical tool relative to a medical implant, comprising:

a) a medical tool; and b) a detection unit, in particular a camera unit, for detecting a marker device attached to a positioning guide for positioning of a medical implant to an anatomical structure, wherein the marker device is in particular the marker device according to any one of embodiments I to P, c) wherein the medical tool and the detection unit have a predetermined and advantageously fixed spatial relationship relative to each other.

S. The system according to the preceding embodiment, comprising a navigation information output unit which comprises in particular an image output unit such as a monitor.

T. The system according to the preceding embodiment, wherein the detection unit and the navigation output unit are combined in a single device, for example a mobile device such as a mobile phone, and are operatively connected to the computer of embodiment D.

U. The system according to any one of the three preceding embodiment, comprising a detection unit holder for holding the detection unit in a predetermined, in particular fixed, spatial relationship relative to the tool driving unit.

V. A system, comprising:

a) at least one of the positioning guide according to embodiments O and the system according to any one of the four preceding embodiments;

b) a medical implant which is connectable, in particular connected, to the connecting section of the positioning guide.

DEFINITIONS

In the following, definitions are disclosed which define the meaning of specific terminology used in the present disclosure. These definitions also form part of the present disclosure.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, in particular computer-readable data storage medium comprising computer-usable, in particular computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, in particular a data processing device comprising a digital processor (central processing unit or CPU) which executes the computer program elements and optionally a volatile memory (in particular, a random access memory or RAM) for storing data used for and/or produced by executing the computer program elements. Within the framework of the present invention, a computer-usable, in particular computer-readable data storage medium can be any data storage medium which can include, store, communicate, propagate or transport the program for use on or in connection with the instruction-executing system, apparatus or device. The computer-usable, in particular computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or vibration element incorporated into an instrument).

It is the function of a marker to be detected by a marker detection device (for example, a camera or an ultrasound receiver or analytical devices, like CT or MRI or an image detection unit such as a camera, in particular a digital camera operating in at least one of the visual and the infrared wavelength range of the electromagnetic spectrum), such that its spatial position (i.e. its spatial location and/or alignment or orientation, respectively) can be ascertained. The detection device is in particular part of a navigation system. The markers can be active markers. An active marker can for example emit electromagnetic radiation and/or waves, wherein said radiation can be in the infrared, visible and/or ultraviolet spectral range. The marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can also, however, exhibit a cornered—for example, cubic—shape.

A marker device can for example be a reference star or a pointer or one marker or more than one (individual) markers which are preferably in a predetermined spatial relationship. A marker device comprises one, two, three or more markers which are in case of two or more markers in a predetermined spatial relationship. This predetermined spatial relationship is in particular known to a navigation system and for example stored in a computer of the navigation system. According to a further example, a marker device can be a two-dimensional (graphical) code such as a bar code or a QR-code® as is also mentioned in the general description of the present invention, which code is in particular present (for example printed or engraved) on a surface such as a label or a part of an in particular medical device.

A navigation system, in particular a surgical navigation system, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) in particular comprises a processor (CPU), a working memory, advantageously an indicating device for issuing an indication signal (for example, a visual indicating device such as a monitor and/or an audio indicating device such as a loudspeaker and/or a tactile indicating device such as a vibrator) and advantageously a permanent data memory, wherein the data processing device processes navigation data forwarded to it by the receiver and can advantageously output guidance information to a user via the indicating device. The navigation data can be stored in the permanent data memory and for example compared with data stored in said memory beforehand. In accordance with the present invention, a navigation system is preferably embodied by a mobile device such as a mobile phone or a personal digital assistant, wherein the at least one marker device is detectable in particular by image analysis (such as an image segmentation algorithm) of an image generated by the receiver which is in particular the above-described detection unit such as a camera of the mobile device. The camera may be operative in at least one of the visual electromagnetic wavelength spectrum and the infrared electromagnetic wavelength spectrum. Preferably, the camera is however operative in the visual electromagnetic wavelength spectrum.

A marker holder is understood to mean an attaching device for an individual marker which serves to attach the marker to an instrument, a part of the body and/or a holding element of a reference star, wherein it can be attached such that it is stationary and advantageously such that it can be detached. A marker holder can for example be rod-shaped and/or cylindrical. A fastening device (such as for instance a latching mechanism) for the marker device can be provided at the end of the marker holder which faces the marker and assists in placing the marker device on the marker holder in a force fit and/or positive fit.

The method in accordance with the invention is in particular a data processing method. The data processing method is preferably performed using technical means, in particular a computer. The data processing method is in particular executed by or on the computer. The computer in particular comprises a processor and a memory in order to process the data, in particular electronically and/or optically. The calculating steps described are in particular performed by a computer. Determining steps or calculating steps are in particular steps of determining data within the framework of the technical data processing method, in particular within the framework of a program. A computer is in particular any kind of data processing device, in particular electronic data processing device. A computer can be a device which is generally thought of as such, for example desktop PCs, notebooks, netbooks, etc., but can also be any programmable apparatus, such as for example a mobile phone or an embedded processor. A computer can in particular comprise a system (network) of "sub-computers", wherein each sub-computer represents a computer in its own right. The term "computer" includes a cloud computer, in particular a cloud server. The term "cloud computer" includes a cloud computer system which in particular comprises a system of at least one cloud computer and in particular a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing" which describes computation, software, data access and storage services which do not require the end user to know the physical location and/or configuration of the computer delivering a specific service. In particular, the term "cloud" is used as a metaphor for the internet (world wide web). In particular, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer in particular comprises interfaces in order to receive or output data and/or perform an analogue-to-digital conversion. The data are in particular data which represent physical properties and/or are generated from technical signals. The technical signals are in particular generated by means of (technical) detection devices (such as for example devices for detecting marker devices) and/or (technical) analytical devices (such as for example devices for performing imaging methods), wherein the technical signals are in particular electrical or optical signals. The technical signals in particular represent the data received or outputted by the computer.

The expression "acquiring data" encompasses in particular (within the framework of a data processing method) the scenario in which the data are determined by the data processing method or program. Determining data in particular encompasses measuring physical quantities and transforming the measured values into in particular digital data and/or computing the data by means of a computer, in particular computing the data within the method of the invention. The meaning of "acquiring data" in particular also encompasses the scenario in which the data are received or retrieved by the data processing method or program, for example from another program, a previous method step or a data storage medium, in particular for further processing by the data processing method or program. Thus, "acquiring data" can also for example mean waiting to receive data and/or receiving the data. The received data can for example be inputted via an interface. "Acquiring data" can also mean that the data processing method or program performs steps in order to (actively) receive or retrieve the data from a data source, for instance a data storage medium (such as for example a ROM, RAM, database, hard disc, etc.) or via the interface (for instance, from another computer or a network). The data can achieve the state of being "ready for use" by performing an additional step before the acquiring step. In accordance with this additional step, the data are generated in order to be acquired. The data are in particular detected or captured (for example, by an analytical device). Alternatively or additionally, the data are inputted in accordance with the additional step, for instance via interfaces. The data generated can in particular be inputted (for instance, into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. Thus, "acquiring data" can also involve commanding a device to obtain and/or provide the data to be acquired. The acquiring step in particular does not involve an invasive step which would represent a substantial physical interference with the body requiring professional medical expertise to be carried out and entailing a substantial health risk even when carried out with the required professional care and expertise. Acquiring, in particular determining, data in particular does not involve a surgical step and in particular does not involve a step of treating a human or animal body using surgery or therapy. This also applies in particular to any steps directed to determining data. In order to distinguish the different data used by the present method, the data are denoted (i.e. referred to) as "XY data" and the like and are defined by the information which they describe which is preferably called "XY information".

SHORT DESCRIPTION OF THE FIGURES

In the following, the invention is described with reference to the figures which represent preferred embodiments of the invention without limiting the invention to the specific features shown in the figures.

Figure 1:
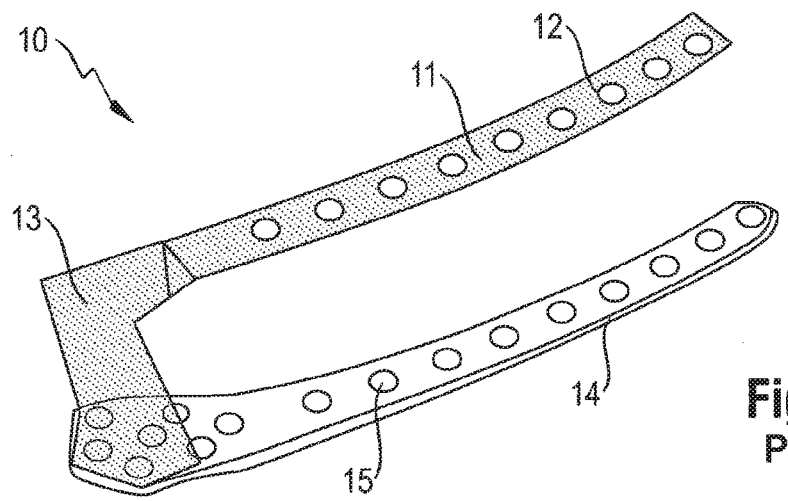
FIG. 1 shows a positioning guide according to the state of the art.

As shown in FIG. 1, a positioning guide 10 in accordance with the state of the art comprises a tool guide 11 having openings 12 serving as implant attachment units through which a tool is inserted, for example a screwdriver is inserted into the openings for screwing screws representing fixture for fastening a medical implant 14 to a structure. The positioning guide 10 also comprises a connecting section 13 for connecting the tool guide 11 to the medical implant 14 which is embodied by a femoral plate. The implant 14 (femoral plate) has implant attachment units 15 embodied by holes in the implant 14 through which the tool and/or a fastener for fastening the implant 14 to an anatomical structure are led. The openings 12 are positioned on the tool guide 11 such that, when viewed from above, they lie over the holes 15.

By way of a predetermined and fixed spatial relationship between the tool guide 11, connecting section guide and implant 14, it thus is possible to lead a tool through the openings 12 in order to aim at the positions of the holes 15 so that, for example, a drill can be led through the openings 12 and the holes 15 in order to drill openings for example screws into a structure lying under the implant 14. In particular, the openings 12 allow to aim the tool at the positions of the holes 15. However, in the positioning guide 10 according to the state of the art, the tool guide 11 can only be used for a specific type of implant 14 since the openings 12 have to be positioned at predetermined positions which, when viewed from the above, coincide with the positions of the holes 15 in the direction along which the tool is to be inserted into holes 15. Producing such a tool guide 11 therefore is costly since the positions of the openings 12 have to be chosen with high precision and it is therefore desirable to re-use the tool guide 11.

Figure 2:
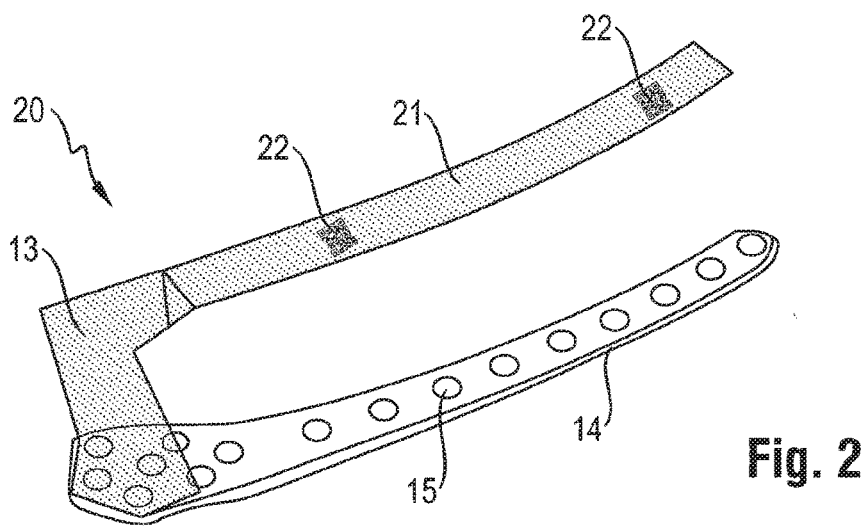
FIG. 2 shows a positioning guide in accordance with an embodiment of the present invention.

FIG. 2 shows a positioning guide 20 in accordance with an embodiment of the present invention. The positioning guide 20 comprises a marker carrying unit 21 having a longitudinal shape, on the surface of which two two-dimensional markers 22 are attached at preferably predetermined positions. The marker carrying unit 21 has a predetermined and preferably fixed spatial relationship (in particular, at least one of position and orientation) relative to the connecting section 13 to which it is fastened. The connecting section 13 is fastened with a predetermined and preferably fixed spatial relationship (i.e. at least one of position and orientation) to an implant 14 having holes 15 through which fasteners are led in order to fasten the medical implant 14 to an anatomical structure. The medical implant 14 is again embodied by a femoral plate.

Figure 3:
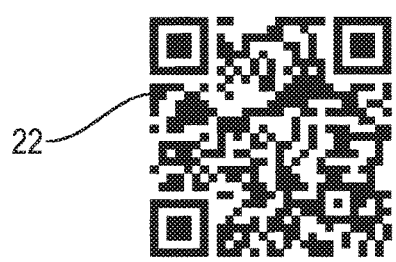
FIG. 3 shows a two-dimensional marker device.

The marker devices 22 are shown in detail in FIG. 3. The marker devices 22 are embodied by QR-codes® which may be printed or engraved (e.g. etched) onto the in particular upper surface of the marker carrying unit 21. Alternatively, the marker devices 22 may be printed on a label which is adhered to the respective surface of the marker carrying unit 21.

Figure 4:
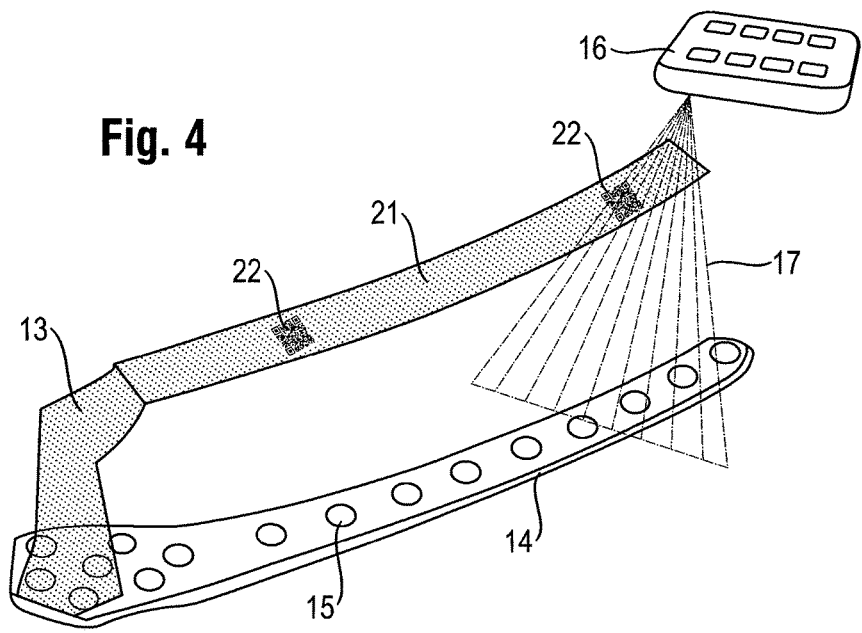
FIG. 4 shows a positioning guide in accordance with the invention being detected by a detection unit.
Figure 5:
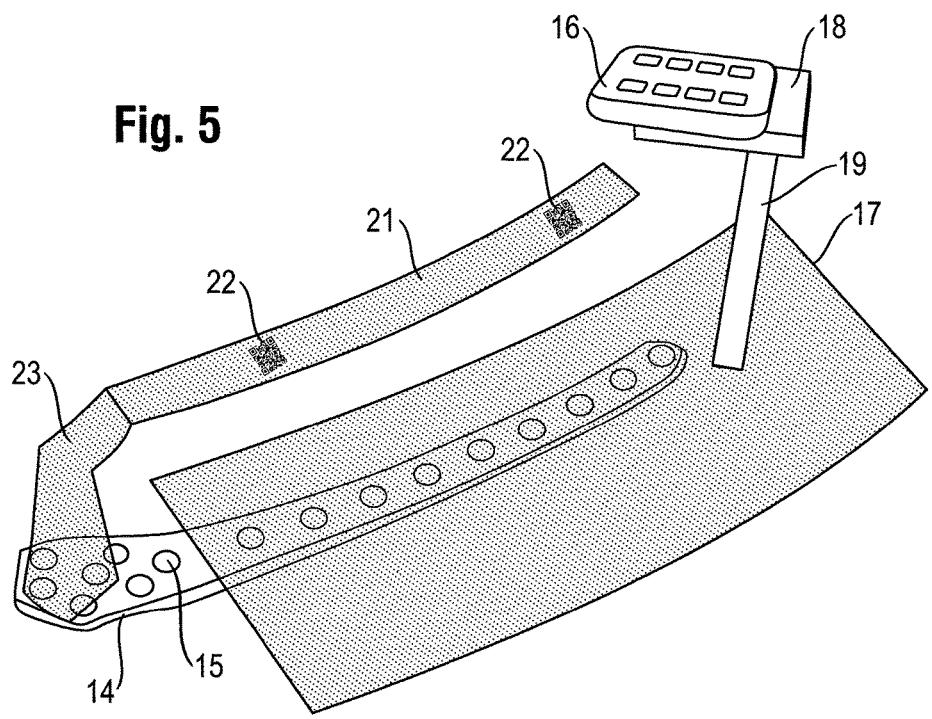
FIG. 5 shows a positioning guide in accordance with an embodiment of the present invention being detected by a detection unit having a fixed spatial relationship relative to a tool driving unit and a tool.
Figure 6:
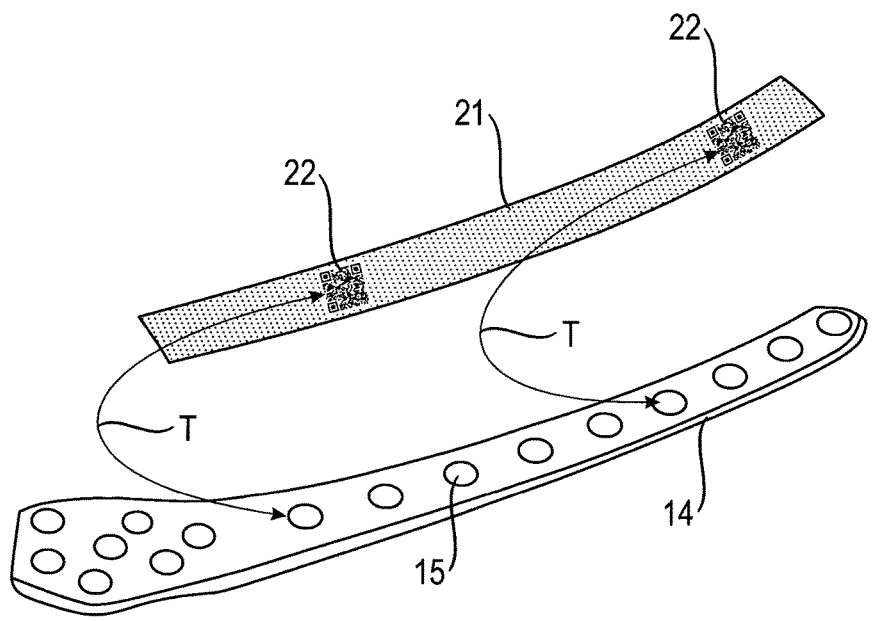
FIG. 6 illustrates the implant attachment unit information.

FIG. 4 illustrates detection of the marker devices 22 by a detection unit 16 embodied by a mobile phone having a camera having an in particular conical detection area 17 for image detection of the marker devices 22. The detection area 17 is defined by i.a. the optical properties of the camera installed in the mobile phone. FIG. 5 shows the detection unit 16 fitted into a detection unit holder 18. The detection unit holder 18 is in this case mechanically attached to the tool 19 which is embodied by a drill in a predetermined and advantageously fixed spatial relationship relative to the detection unit 16. Using the positioning guide 20 in accordance with the present invention, the drill 19 need not be fed through openings 12 (which anyway are not present in the marker carrying unit 21). Rather, the marker carrying unit 21 advantageously does not lie over the holes 15 of the medical implant 14 when viewed in a direction in which the drill 19 is to be positioned into holes 15 (in this disclosure also termed tool application direction), in particular when viewed from above the medical implant 14 when the latter is for example in the position in which it is to be attached to the anatomical structure. Rather, it suffices to retrieve the implant attachment unit information encoded in the two-dimensional marker devices 22 by way of optical detection with the detection unit 16. Detection of the marker devices 22 also provides information about the position of the marker devices 22 relative to the tool 19 by way of the predetermined and advantageously fixed spatial relationship between the detection unit 16 and the tool 19. The implant attachment unit information in this case is embodied by a transformation T representing a coordinate transformation (in particular, a mapping) between the position of each marker device 22 and the position of each implant attachment unit embodied by a whole 15. The arithmetic function defining the transformation T is predetermined for each type of implant 14 and encoded in the graphical pattern represented by the marker devices 22.

Based on retrieving the implant attachment unit information by optical detection of the marker devices 22, a graphical output is rendered on the display device of the mobile phone representing the detection unit 16. The graphical output informs the user about the spatial relationship (in particular, the orientation) of the tool 19 relative to the positions of the holes 15. The user is thus supported in positioning the tool correctly in order to for example drill holes into an anatomical structure lying beneath the positions of the implant attachment units 15.

Figure 7:
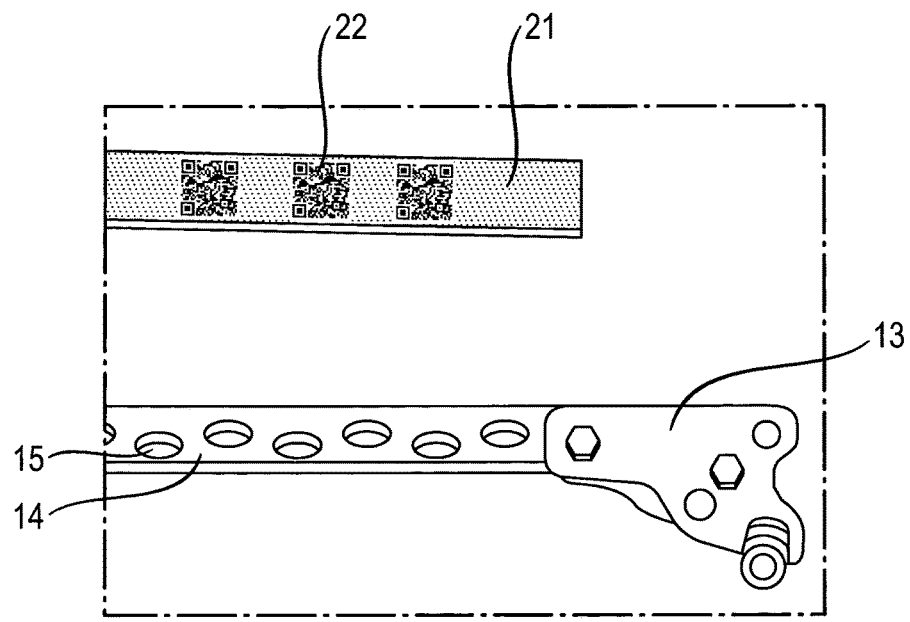
FIG. 7 shows a system comprising a positioning guide in accordance with an embodiment of the invention and a medical implant.

FIG. 7 shows a prototype of the inventive positioning guide 20. The marker carrying unit 21 and the connecting section 13 are formed integrally and a plurality of labels each provided with a two-dimensional marker device 22 embodied by a QR-code® are attached to the upper surface of the marker carrying unit 21. The connecting section 13 is screwed to the medical implant 14 having holes 15. In the configuration shown in FIG. 7, the medical implant 14 can be led through a small incision for example in the soft tissue surrounding the femur, while the connecting section 13 and the marker carrying unit 21 are attached to the medical implant 14. While the medical implant 14 then is no longer visible to the user and/or the detection unit 16 (since it is lying under the closed part of the tissue), the marker devices 22 are visible to the user and/or the detection device 16. It thus is possible to navigate the tool 19 using the detection device 16 for detecting the marker devices 22 to positions for example on the outer surface of the patient's skin which lie over the positions of the holes 15 in order to drill holes into the anatomical structure (the femur) lying under the holes 15. These drilled holes may then serve to insert for example screws through the medical implant 14 in order to fix the medical implant 14 to the femur.

The invention claimed is:

1. A method comprising:
   detecting a marker device having a fixed spatial relationship relative to an associated medical device;
   acquiring information about the geometry of the associated medical device and information about the spatial relationship of the marker device relative to the associated medical device, wherein the information about the geometry of the associated medical device is acquired based on:
      analyzing an image of the associated medical device and the marker device and comparing the result of the image analysis with predetermined information about the geometry of a plurality of associated medical devices which is contained in a database in order to acquire the information about the geometry of the associated medical device, wherein the detecting the marker device comprises detecting a pattern which encodes information for accessing the information about the geometry of the associated medical device;
   notifying positions of specific parts of the associated medical device to a navigation system; and
   determining, based on the information about the geometry of the associated medical device, a spatial relationship between the associated medical device and a tracked tool for aiming the tracked tool at the associated medical device.

2. The method according to claim 1, wherein:
   the associated medical device is an implant attachment unit.

3. The method according to claim 1, wherein the detecting the pattern comprises:
   detecting a two-dimensional graphical pattern.

4. The method according to claim 1, wherein:
   the associated medical device does not have a predetermined spatial relationship relative to at least one of a tracking device for tracking the marker device and a display device for displaying the results of the tracking; and
   the associated medical device is associated with a further marker device having a predetermined spatial relationship relative to the associated medical device.

5. The method according to claim 4, wherein the associated medical device comprises a specific medical device.

6. The method according to claim 1, further comprising:
   tracking the marker device by a tracking device which is comprised in a handheld device comprising a mobile media player or a mobile phone, and which includes a camera which is sensitive in the visual wavelength range.

7. The method according to claim 1, wherein:
   the associated medical device comprises a drill guide or an implant.

8. The method according to claim 1, further comprising:
   determining the geometry of the associated medical device based on the notified positions.

9. A non-transitory computer-readable program storage medium storing a computer program which, when running on a processor of a computer or when loaded into a memory of a computer having the processor, causes the computer to perform a computer implemented medical data processing method, comprising:
   detecting a marker device having a fixed spatial relationship relative to an associated medical device;
   acquiring information about the geometry of the associated medical device and information about the spatial relationship of the marker device relative to the associated medical device, wherein the information about the geometry of the associated medical device is acquired based on:
      analyzing an image of the associated medical device and the marker device and comparing the result of the image analysis with predetermined information about the geometry of a plurality of associated medical devices which is contained in a database in order to acquire the information about the geometry of the associated medical device, wherein the detecting the marker device comprises detecting a pattern which encodes information for accessing the information about the geometry of the associated medical device;
   notifying positions of specific parts of the associated medical device to a navigation system; and determining, based on the information about the geometry of the associated medical device, a spatial relationship between the associated medical device and a tracked tool for aiming the tracked tool at the associated medical device.

10. A computer comprising:

a processor; and a non-transitory program storage medium storing a computer program which, when running on the processor of the computer or when loaded into the non-transitory program storage medium of the computer, causes the computer to perform a computer implemented medical data processing method, the computer implemented medical data processing method comprising:

detecting a marker device having a fixed spatial relationship relative to an associated medical device:

acquiring information about a geometry of an associated medical device and information about a spatial relationship of a marker device relative to the associated medical device, wherein the information about the geometry of the associated medical device is acquired based on:

analyzing an image of the associated medical device and the marker device and comparing the result of the image analysis with predetermined information about the geometry of a plurality of associated medical devices which is contained in a database in order to acquire the information about the geometry of the associated medical device, wherein the detecting the marker device comprises detecting a pattern which encodes information for accessing the information about the geometry of the associated medical device;

notifying positions of specific parts of the associated medical device to a navigation system; and determining, based on the information about the geometry of the associated medical device, a spatial relationship between the associated medical device and a tracked tool for aiming the tracked tool at the associated medical device.

11. A medical system comprising:

a marker device having a fixed spatial relationship relative to an associated medical device; and a computer comprising a processor and a non-transitory program storage medium storing a computer program which, when running on the processor of the computer or when loaded into the non-transitory program storage medium of the computer, causes the computer to perform a computer implemented medical data processing method, the medical data processing method comprising:

detecting the marker device:

acquiring information about the geometry of the associated medical device and information about the spatial relationship of the marker device relative to the associated medical device, wherein the information about the geometry of the associated medical device is acquired based on:

analyzing an image of the associated medical device and the marker device and comparing the result of the image analysis with predetermined information about the geometry of a plurality of associated medical devices which is contained in a database in order to acquire the information about the geometry of the associated medical device, wherein the detecting the marker device comprises detecting a pattern which encodes information for accessing the information about the geometry of the associated medical device;

notifying positions of specific parts of the associated medical device to a navigation system; and determining, based on the information about the geometry of the associated medical device, a spatial relationship between the associated medical device and a tracked tool for aiming the tracked tool at the associated medical device.

* * * * *

UNITED STATES PATENT AND TRADEMARK OFFICE
CERTIFICATE OF CORRECTION

Page 1 of 1

PATENT NO.         : 9,987,093 B2
APPLICATION NO.    : 14/902051
DATED              : June 5, 2018
INVENTOR(S)        : Georg Christian, Thomas Feilkas and Ingmar Hook It is certified that error appears in the above-identified patent and that said Letters Patent is hereby corrected as shown below:

Column 01, Line 06 and Line 07:
--PCT/EP2013/064343 filed Sep.25, 2012--
Should read:
--PCT/EP2013/064343 filed July 08, 2013--

Signed and Sealed this
Thirty-first Day of July, 2018

Andrei Iancu
*Director of the United States Patent and Trademark Office*